US009080201B2

(12) United States Patent
Katayama et al.

(10) Patent No.: US 9,080,201 B2
(45) Date of Patent: Jul. 14, 2015

(54) METHOD FOR MEASURING CHOLESTEROL IN HDL SUBFRACTION, AND REAGENTS AND KIT THEREFOR

(75) Inventors: Yuki Katayama, Sunto-gun (JP); Hiroyuki Sugiuchi, Kumamoto (JP); Kazumi Matsushima, Kumamoto (JP)

(73) Assignees: KYOWA MEDEX CO., LTD., Tokyo (JP); KUMAMOTO HEALTH SCIENCE UNIVERSITY, Kumamoto (JP)

( * ) Notice: Subject to any disclaimer, the term of this patent is extended or adjusted under 35 U.S.C. 154(b) by 0 days.

(21) Appl. No.: 14/002,816

(22) PCT Filed: Mar. 15, 2012

(86) PCT No.: PCT/JP2012/001820
§ 371 (c)(1),
(2), (4) Date: Sep. 3, 2013

(87) PCT Pub. No.: WO2012/124340
PCT Pub. Date: Sep. 20, 2012

(65) Prior Publication Data
US 2013/0344518 A1 Dec. 26, 2013

(30) Foreign Application Priority Data
Mar. 16, 2011 (JP) ................................. 2011-057959

(51) Int. Cl.
*C12Q 1/60* (2006.01)
*G01N 33/92* (2006.01)
(52) U.S. Cl.
CPC . *C12Q 1/60* (2013.01); *G01N 33/92* (2013.01)
(58) Field of Classification Search
None
See application file for complete search history.

(56) References Cited

U.S. PATENT DOCUMENTS

| 5,773,304 | A | 6/1998 | Hino et al. | |
| 5,888,755 | A * | 3/1999 | Miyauchi et al. | 435/11 |
| 2005/0287619 | A1* | 12/2005 | Katayama et al. | 435/11 |
| 2009/0181413 | A1* | 7/2009 | Itoh et al. | 435/11 |
| 2009/0280514 | A1* | 11/2009 | Katayama et al. | 435/11 |
| 2013/0157374 | A1* | 6/2013 | Higuchi et al. | 436/71 |

FOREIGN PATENT DOCUMENTS

| EP | 0 753 583 | | 1/1997 |
| EP | 1 876 243 | | 1/2008 |
| JP | 08-201393 | | 8/1996 |
| JP | 2001-346598 | | 12/2001 |
| JP | 2009-207463 | * | 9/2009 |
| WO | WO 2012/011556 | * | 1/2012 |

OTHER PUBLICATIONS

English translation of JP-2009-207463.*
Hydrolase, The Enzyme List, ExplorEnz Database, Sep. 2010.*
JP-2009-207463-translated, English translation of Japanese Patent 2009-207463.*
Dias, et al., "Dual-Precipitation Method Evaluated for Determination of High-Density Lipoprotein (HDL), HDL2, and HDL3 Cholesterol Concentrations", Clin. Chem., vol. 34, No. 11 (1988) 2322-27.
Gidez, et al., "Separation and quantitation of subclasses of human plasma high density lipoproteins by a simple precipitation procedure", Journal of Lipid Research, vol. 23, No. 8 (1982) 1206-23.
Hirano, et al., "A simple and precise method for measuring HDL-cholesterol subfractions by a single precipitation followed by homogenous HDL-cholesterol assay", Journal of Lipid Research, vol. 49, No. 5 (2008) 1130-36.
Kalju, et al., "Untersuchungen zu elner Polyethylenglykol-Präzipitationsmethode (Quantolip) zur Bestimmung von HDL2-, HDL3- und Gesamt-HDL-Cholesterin im Serum", Ärztl. Lab., vol. 35, (1989) 93-100.
Matsushima et al., "HDL Abunkaku Cholesterol no Chokusetsuho no Kaihatsu to Rinsho Oyo", Japanese Journal of Clinical Laboratory Automation, vol. 36, No. 4 (2011) 622.
Matsushima, et al., "Development and Clinical Application of Direct Measurement Method for HDL2 and HDL3 cholesterols", Rinsho Kagaku, vol. 40, Suppl. 1 (2011) 208 (33).
Patech, et al., "A Dual-Precipitation Method for Measurement of Cholesterol in High-Density Lipoprotein Subfractions HDL2 and HDL3 in Human Plasma", Clin. Chem., vol. 35, No. 2 (1989) 265-70.
Takamatsu, et al., "Studies on the Measurement of HDL2-, HDL3-Cholesterol by a Precipitation Procedure with Dextran Sulfate, and its Clinical Application", Japanese Journal of Clinical Pathology, vol. XXXII, No. 11 (1984) 1235-41.
Whitaker, et al., "Simplified Methods for Measuring Cholesterol Concentrations of High-Density Lipoprotein Subclasses in Serum Compared", Clin. Chem., vol. 32, No. 7 (1986) 1274-78.
Yamauchi, et al., "Evaluation of Reactivity Using Direct Assay Methods for High Density Lipoprotein Cholesterol", Rinsho Kagaku, vol. 26, No. 3 (1997) 150-56.
Finley, et al., "Cholesterol in High-Density Lipoprotein: Use of Mg2+/Dextran Sulfate in Its Enzymic Measurement", Clin. Chem., vol. 24, No. 6 (1978) 931-33.
Talameh, et al., "Measurement of total HDL, HDL2 and HDL3 by dextran sulfate—MgCl2 precipitation technique in human serum", Clinica Chimica Acta, vol. 158, No. 1 (1986) 33-41.
Warnick, et al., "Comparison of Improved Precipitation Methods for Quantification of High-Density Lipoprotein Cholesterol", Clin. Chem., vol. 31, No. 2 (1985) 217-22.
Warnick, et al., "Dextran Sulfate-Mg2+ Precipitation Procedure for Quantitation of High-Density-Lipoprotein Cholesterol", Clin. Chem., vol. 28, No. 6 (1982) 1379-88.

* cited by examiner

*Primary Examiner* — Taeyoon Kim
*Assistant Examiner* — Srikanth Patury
(74) *Attorney, Agent, or Firm* — Fitzpatrick, Cella, Harper & Scinto

(57) ABSTRACT

The present invention provides a method for simply and precisely measuring cholesterol in an HDL subfraction contained in a sample. This is a method for measuring cholesterol in HDL3 contained in a sample, which comprises reacting a sample with (1) a combination of a cholesterol ester hydrolase and a cholesterol oxidase or (2) a combination of a cholesterol ester hydrolase, an oxidized coenzyme and a cholesterol dehydrogenase in an aqueous medium containing: (a) a divalent metal salt; (b) an alkali metal salt selected from the group consisting of a sulfate, a nitrate, a carbonate, an acetate and a halide; and (c) dextran sulfate or a salt thereof, and measuring a substance formed or consumed in the reaction without separating and removing lipoproteins other than HDL3.

5 Claims, No Drawings

METHOD FOR MEASURING CHOLESTEROL IN HDL SUBFRACTION, AND REAGENTS AND KIT THEREFOR

This application is a national phase of PCT Application No. PCT/JP2012/001820 filed Mar. 15, 2012, which in turn claims benefit of JP 2011-057959 filed Mar. 16, 2011.

TECHNICAL FIELD

The present invention relates to a method, a reagent and a kit for measuring cholesterol in an HDL subfraction contained in a sample.

BACKGROUND ART

High-density lipoprotein (HDL) is one of lipoproteins, and it has a specific gravity from 1.063 to 1.210. Cholesterol in HDL (HDL-C) has been known as a negative risk factor for coronary heart disease (CHD). In recent years, there has been an increasing interest in the clinical significance of HDL subfractions, HDL2 and HDL3. HDL2 is a lipoprotein having a specific gravity from 1.063 to 1.125, whereas HDL3 is a lipoprotein having a specific gravity from 1.125 to 1.210.

Nascent HDL secreted from the liver or the intestine adheres to the peripheral cell membrane, and it absorbs free cholesterol therefrom. The thus absorbed free cholesterol is converted to esterified cholesterol by the action of LCAT (lecithin cholesterol acyltransferase) that is present on the surface of HDL, and then, spherical HDL3 is formed having this esterified cholesterol as a core. Then, the amount of the esterified cholesterol is increased in HDL3 by the action of LCAT, and as a result, HDL3 is converted to HDL2.

Cholesterol in HDL2 is metabolized by two pathways. One is a pathway by which cholesterol in HDL2 is directly incorporated into the liver in a state of HDL2 as such and is then excreted as a bile acid. The other is a pathway, by which esterified cholesterol in HDL2 is exchanged with triglycerides contained in triglycerides-rich lipoproteins, such as a very low-density lipoprotein (VLDL), an intermediate density lipoprotein (IDL) and a low-density lipoprotein (LDL), by the action of CETP (cholesterol ester transfer protein), and the esterified cholesterol are transported to the triglycerides-rich lipoproteins (reverse cholesterol transport system).

As a method for measuring cholesterol in an HDL subfraction, a precipitation method comprising a step of separating HDL3 from HDL2 and a homogeneous method that does not comprise a step of separating HDL3 from HDL2 have been known so far.

As a precipitation method, a method for measuring cholesterol in HDL3 contained in a sample by a single separation operation using heparin, divalent metal ions and dextran sulfate (for example, Patent Document 1 and Non-patent Document 1), a method for measuring cholesterol in HDL3 contained in a sample by a double separation operation (for example, Non-patent Documents 2 to 4), and the like have been known. The method for measuring cholesterol in HDL3 contained in a sample by the single separation operation is a method comprising agglutinating lipoproteins in a sample, other than HDL3, then separating and removing them, and then measuring cholesterol in the thus obtained HDL3. The method for measuring cholesterol in HDL3 contained in a sample by the double separation operation is a method comprising first agglutinating lipoproteins in a sample, other than HDL, then removing lipoproteins other than HDL by centrifugation, then agglutinating HDL2 in the obtained supernatant containing HDL, then removing the HDL2 by centrifugation, then recovering HDL3 contained in the supernatant, and then measuring cholesterol in the thus obtained HDL3.

As a homogeneous method, a method using an enzyme exhibiting high specificity to HDL and a nonionic surfactant having an HLB value of 17 or greater has been known (for example, Patent Document 2).

There is a need for a method for simply and precisely measuring cholesterol in an HDL subfraction contained in a sample without performing complicated operations such as centrifugation.

PRIOR ART DOCUMENTS

Patent Documents

Patent Document 1: Japanese unexamined Patent Application Publication No. 2009-207463
Patent Document 2: Japanese unexamined Patent Application Publication No. 2001-346598

Non-Patent Documents

Non-patent Document 1: Journal of Lipid Research, Vol. 49, No. 5 (2008) 1130-36
Non-patent Document 2: Clinical Chemistry, Vol. 34, No. 11 (1988) 2322-27
Non-patent Document 3: Clinical Chemistry, Vol. 35, No. 2 (1989) 265-70
Non-patent Document 4: Journal of Lipid Research, Vol. 23, No. 8 (1982) 1206-23

SUMMARY OF THE INVENTION

Object to be Solved by the Invention

It is an object of the present invention to provide a method, a reagent, and a kit for simply and precisely measuring cholesterol in an HDL subfraction contained in a sample.

Means to Solve the Object

As a result of intensive studies directed towards achieving the above-mentioned object, the present inventors have found that cholesterol in HDL3 can be measured using cholesterol-measuring enzymes, a divalent metal salt, a specific alkali metal salt, and dextran sulfate or a salt thereof without separating and removing lipoproteins other than HDL3 to complete the present invention. Specifically, the present invention relates to the following [1] to [19]:

[1] A method for measuring cholesterol in HDL3 contained in a sample, which comprises
reacting the sample with (1) a combination of a cholesterol ester hydrolase and a cholesterol oxidase or (2) a combination of a cholesterol ester hydrolase, an oxidized coenzyme and a cholesterol dehydrogenase in an aqueous medium containing (a) a divalent metal salt, (b) an alkali metal salt selected from the group consisting of a sulfate, a nitrate, a carbonate, an acetate and a halide, and (c) dextran sulfate or a salt thereof, and
measuring a substance formed or consumed in the reaction without separating and removing lipoproteins other than HDL3.
[2] The method according to [1] above, wherein the divalent metal salt is a magnesium salt or a calcium salt.
[3] The method according to [1] or [2] above, wherein the concentration of the dextran sulfate or a salt thereof in the reaction solution is 0.75 to 2.6 g/L.

[4] The method according to anyone of [1] to [3] above, wherein the concentration of divalent metal ions derived from the divalent metal salt in the reaction solution is 12 to 20 mmol/L, and the concentration of alkali metal ions derived from the alkali metal salt in the reaction solution is 5 to 21 mmol/L.

[5] A method for measuring cholesterol in HDL2 contained in a sample, which comprises the following steps:
(1) a step of measuring cholesterol in a high-density lipoprotein (HDL) contained in the sample;
(2) a step of measuring cholesterol in HDL3 contained in the sample by the method according to any one of [1] to [4] above; and
(3) a step of subtracting a measurement value obtained by the measurement in the step (2) from a measurement value obtained by the measurement in the step (1).

[6] A reagent for measuring cholesterol in HDL3 contained in a sample by the method according to any one of [1] to [4] above without separating and removing lipoproteins other than HDL3, wherein the reagent comprises a cholesterol ester hydrolase, a cholesterol oxidase, (a) a divalent metal salt, (b) an alkali metal salt selected from the group consisting of a sulfate, a nitrate, a carbonate, an acetate and a halide, (c) dextran sulfate or a salt thereof, and a reagent for measuring hydrogen peroxide.

[7] A reagent for measuring cholesterol in HDL3 contained in a sample by the method according to any one of [1] to [4] above without separating and removing lipoproteins other than HDL3, wherein the reagent comprises a cholesterol ester hydrolase, an oxidized coenzyme, a cholesterol dehydrogenase, (a) a divalent metal salt, (b) an alkali metal salt selected from the group consisting of a sulfate, a nitrate, a carbonate, an acetate and a halide, and (c) dextran sulfate or a salt thereof.

[8] The reagent according to [7] above, which further comprises a reagent for measuring a reduced coenzyme.

[9] The reagent according to any one of [6] to [8] above, wherein the divalent metal salt is a magnesium salt or a calcium salt.

[10] The reagent according to any one of [6] to [9] above, which comprises the dextran sulfate or a salt thereof in such a content that the concentration thereof in the reaction solution is 0.75 to 2.6 g/L.

[11] The reagent according to any one of [6] to [10] above, which comprises the divalent metal salt in such a content that the concentration of divalent metal ions derived from the divalent metal salt in the reaction solution is 12 to 20 mmol/L, and which comprises the alkali metal salt in such a content that the concentration of alkali metal ions derived from the alkali metal salt in the reaction solution is 5 to 21 mmol/L.

[12] A kit for measuring cholesterol in HDL3 contained in a sample by the method according to any one of [1] to [4] above without separating and removing lipoproteins other than HDL3, which comprises a first reagent and a second reagent, wherein
(a) a divalent metal salt, (b) an alkali metal salt selected from the group consisting of a sulfate, a nitrate, a carbonate, an acetate and a halide, and (c) dextran sulfate or a salt thereof are comprised in the first reagent,
a cholesterol oxidase is comprised in the second reagent,
a reagent for measuring hydrogen peroxide is comprised in either the first reagent or the second reagent, or in both of the first and second reagents, and
a cholesterol ester hydrolase is comprised in either the first reagent or the second reagent, or in both of the first and second reagents.

[13] A kit for measuring cholesterol in HDL3 contained in a sample by the method according to any one of [1] to [4] above without separating and removing lipoproteins other than HDL3, which comprises a first reagent and a second reagent, wherein
(a) a divalent metal salt, (b) an alkali metal salt selected from the group consisting of a sulfate, a nitrate, a carbonate, an acetate and a halide, and (c) dextran sulfate or a salt thereof are comprised in the first reagent,
a cholesterol dehydrogenase is comprised in the second reagent,
an oxidized coenzyme is comprised in either the first reagent or the second reagent, or in both of the first and second reagents, and
a cholesterol ester hydrolase is comprised in either the first reagent or the second reagent, or in both of the first and second reagents.

[14] The kit according to [13] above, which further comprises a reagent for measuring a reduced coenzyme in either the first reagent or the second reagent, or in both of the first and second reagents.

[15] The kit according to any one of [12] to [14] above, wherein the divalent metal salt is a magnesium salt or a calcium salt.

[16] The kit according to any one of [12] to [15] above, which comprises the dextran sulfate or a salt thereof in such a content that the concentration thereof in the reaction solution is 0.75 to 2.6 g/L.

[17] The kit according to any one of [12] to [16] above, which comprises the divalent metal salt in such a content that the concentration of divalent metal ions derived from the divalent metal salt in the reaction solution is 12 to 20 mmol/L, and which comprises the alkali metal salt in such a content that the concentration of alkali metal ions derived from the alkali metal salt in the reaction solution is 5 to 21 mmol/L.

[18] A kit for measuring cholesterol in HDL2 contained in a sample, which comprises the reagent for measuring cholesterol in HDL3 according to any one of [6] to [11] above and a reagent for measuring HDL cholesterol.

[19] A kit for measuring cholesterol in HDL2 contained in a sample, which comprises the first reagent and second reagent of the kit for measuring cholesterol in HDL3 according to any one of [12] to [17] above and a reagent for measuring HDL cholesterol.

Effect of the Invention

According to the present invention, there are provided a method, a reagent, and a kit for simply and precisely measuring cholesterol in an HDL subfraction contained in a sample.

MODE OF CARRYING OUT THE INVENTION

<Method for Measuring Cholesterol in HDL3>

The method for measuring cholesterol in an HDL3 (hereinafter abbreviated as HDL3-C) contained in a sample of the present invention is a method, which does not need to separate and remove lipoproteins using a physical method such as centrifugation. In addition, the measurement method of the present invention is a method for measuring HDL3-C contained in a sample without removing cholesterols in lipoproteins other than HDL3 contained in the sample before the measurement of HDL3-C.

The method for measuring HDL3-C of the present invention comprises reacting a sample with cholesterol-measuring enzymes in an aqueous medium containing (a) a magnesium salt or a calcium salt, (b) an alkali metal salt selected from the group consisting of a sulfate, a nitrate, a carbonate, an acetate and a halide, and (c) dextran sulfate or a salt thereof, and measuring a substance formed or consumed in the reaction without separating and removing lipoproteins other than HDL3. Examples of the cholesterol-measuring enzymes include a combination of a cholesterol ester hydrolase and a cholesterol oxidase, and a combination of a cholesterol ester hydrolase, an oxidized coenzyme and a cholesterol dehydrogenase.

The measurement method of the present invention comprises the following steps (1) to (4):

(1) a step of reacting a sample with cholesterol-measuring enzymes in an aqueous medium containing (a) a divalent metal salt, (b) an alkali metal salt selected from the group consisting of a sulfate, a nitrate, a carbonate, an acetate and a halide, and (c) dextran sulfate or a salt thereof;

(2) a step of measuring a substance formed or consumed in the reaction of the step (1) without separating and removing lipoproteins other than HDL3;

(3) a step of correlating a calibration curve indicating the relationship between the HDL3-C concentration and information amount derived from the aforementioned formed or consumed substance, which has previously been prepared using HDL3-C having a known concentration, with the measurement value obtained in the above described step (2); and (4) a step of determining the concentration of HDL3-C contained in the sample. Herein, examples of the cholesterol-measuring enzymes used in the step (1) include the above described cholesterol-measuring enzymes.

In case a combination of a cholesterol ester hydrolase and a cholesterol oxidase is used as cholesterol-measuring enzymes, an example of the substance in the step (2) that is formed in the reaction of the step (1) is hydrogen peroxide. On the other hand, in case a combination of a cholesterol ester hydrolase, an oxidized coenzyme and a cholesterol dehydrogenase is used as cholesterol-measuring enzymes, an example of the substance in the step (2) that is formed in the reaction of the step (1) is a reduced coenzyme.

In case a combination of a cholesterol ester hydrolase and a cholesterol oxidase is used as cholesterol-measuring enzymes, an example of the substance in the step (2) that is consumed in the reaction of the step (1) is an oxygen molecule.

In the measurement method of the present invention, hydrogen peroxide formed in the reaction of a sample with a cholesterol ester hydrolase and a cholesterol oxidase can be measured using, for example, a hydrogen peroxide electrode or the after-mentioned reagent for measuring hydrogen peroxide.

In the measurement method of the present invention, a reduced coenzyme formed in the reaction of a sample with a cholesterol ester hydrolase, an oxidized coenzyme and a cholesterol dehydrogenase can be measured, for example, by absorptiometry or using the after-mentioned reagent for measuring a reduced coenzyme. The absorptiometry is not particularly limited, as long as it is a method capable of measuring a reduced coenzyme using absorbance. An example of the absorptiometry is a method of measuring the absorbance of a reduced coenzyme with a wavelength around the maximum absorption wavelength of the reduced coenzyme ($\lambda_{max}$=340 nm).

The consumed oxygen molecule can be measured, for example, using an oxygen electrode.

Examples of the sample used in the measurement method of the present invention include whole blood, plasma and serum. Of these, plasma and serum are preferable.

The cholesterol ester hydrolase used in the present invention is not particularly limited, as long as it is an enzyme having ability to hydrolyze a cholesterol ester. Examples of such cholesterol ester hydrolase that can be used in the present invention include: a cholesterol esterase and a lipoprotein lipase, which are derived from animals, plants or microorganisms; and a cholesterol esterase and a lipoprotein lipase, which are produced by genetic engineering methods.

As such cholesterol ester hydrolase, either an unmodified cholesterol ester hydrolase or a chemically modified cholesterol ester hydrolase may be used. In addition, commercially available cholesterol ester hydrolase can also be used.

Examples of such commercially available cholesterol ester hydrolase include a cholesterol esterase (COE-311; manufactured by Toyobo Co., Ltd.), a lipoprotein lipase (LPL-311; Toyobo Co., Ltd.), a cholesterol esterase (CHE "Amano" 3; manufactured by Amano Enzyme Inc.), and a cholesterol esterase (EST "Amano" 2; manufactured by Amano Enzyme Inc.). Moreover, a combination of two or more cholesterol ester hydrolases can also be applied in the present invention.

Examples of a group that modifies a cholesterol ester hydrolase (a chemically modifying group) in the chemical modification of the enzyme include: a group comprising polyethylene glycol as a main component; a group comprising polypropylene glycol as a main component; a group having a copolymer of polypropylene glycol and polyethylene glycol; a group comprising water-soluble polysaccharide; a sulfopropyl group, a sulfobutyl group, a polyurethane group, and a group having a chelating function. Of these, a group comprising polyethylene glycol as a main component is preferable. Examples of such water-soluble polysaccharide include dextran, pullulan, and soluble starch.

Examples of a reagent for chemically modifying a cholesterol ester hydrolase (a chemically modifying reagent) include compounds, which have both the chemically modifying group as described above and a functional group or a structure capable of reacting with an amino group, a carboxyl group, a sulfhydryl group or the like in the enzyme. Examples of the functional group or the structure capable of reacting with an amino group in the enzyme include a carboxyl group, an active ester group (an N-hydroxysuccinimide group, etc.), an acid anhydride, an acid chloride, aldehyde, an epoxide group, 1,3-propane sultone, and 1,4-butane sultone. An example of the functional group or the structure capable of reacting with a carboxyl group in the enzyme is an amino group. Examples of the group or the structure having reactivity with a sulfhydryl group in the enzyme include a maleimide group, disulfide, and an α-haloester (an α-iodoester, etc.)

Commercially available chemically modifying reagents can also be used. Examples of such a commercially available chemically modifying reagent include: Sunbright VFM-4101, Sunbright ME-050AS and Sunbright DE-030AS (all of which are manufactured by NOF Corporation), which have a group comprising polyethylene glycol as a main component and an N-hydroxysuccinimide group; Sunbright AKM series (e.g. Sunbright AKM-1510, etc.), Sunbright ADM series and Sunbright ACM series (all of which are manufactured by NOF Corporation), which have a group comprising polyalkylene glycol as a main component and an acid anhydride structure; EPDX-3400 and M-EPDX-5000 (both of which are manufactured by Sheawater Polymers), which have a group comprising polyethylene glycol as a main component and an epoxide group; and diethylenetriamine-N,N,N',N",N"-pentaacetic acid dianhydride (DTPA anhydride; manufactured by Dojindo Laboratories).

A cholesterol ester hydrolase may be chemically modified by the following method, for example. However, the chemical modification method is not limited thereto. First, a cholesterol ester hydrolase is dissolved in a buffer with a pH value of 8.0 or greater (e.g. HEPES buffer), and a chemically modifying reagent is added at 0 to 55° C. in a molar amount of 0.01 to 500 times the molar amount of the cholesterol ester hydrolase to the obtained solution. The obtained mixture is stirred for 5 minutes to 5 hours. In the enzyme reaction, not only this reaction solution as is, but also a solution, from which an unreacted chemically modifying reagent and the like are removed with an ultrafilter membrane or the like, as necessary, can be used as a chemically modified cholesterol ester hydrolase.

The concentration of the cholesterol ester hydrolase applied in the measurement method of the present invention is not particularly limited, as long as it is a concentration, at which the measurement of HDL3-C of the present invention can be carried out. The concentration of the cholesterol ester hydrolase in the reaction solution is generally 0.001 to 800 kU/L, and preferably 0.01 to 300 kU/L.

The type of the cholesterol oxidase used in the present invention is not particularly limited, as long as it is an enzyme having ability to oxidize cholesterol and form hydrogen peroxide. Examples of such cholesterol oxidase that can be used in the present invention include: a cholesterol oxidase derived from animals, plants or microorganisms; and a cholesterol oxidase, which is produced by genetic engineering methods. There can also be used commercially available products such as a cholesterol oxidase (CHODI; manufactured by Kyowa Hakko Kogyo Co., Ltd.), a cholesterol oxidase (CHODI; manufactured by KIKKOMAN Corporation), a cholesterol oxidase (CHO-CE; manufactured by KIKKOMAN Corporation), a cholesterol oxidase (COO321; manufactured by Toyobo Co., Ltd.), and a cholesterol oxidase (COO322; manufactured by Toyobo Co., Ltd.). Moreover, a combination of two or more cholesterol oxidases can also be applied in the present invention.

As such cholesterol oxidase, either an unmodified enzyme or a chemically modified enzyme may be used. Such a chemically modified cholesterol oxidase can be prepared, for example, by the above described chemical modification method using the above described chemically modifying reagent.

The concentration of the cholesterol oxidase applied in the measurement method of the present invention is not particularly limited, as long as it is a concentration, at which the measurement of HDL3-C of the present invention can be carried out. The concentration of the cholesterol oxidase in the reaction solution is generally 0.001 to 800 kU/L, and preferably 0.01 to 300 kU/L.

The type of the cholesterol dehydrogenase used in the present invention is not particularly limited, as long as it is an enzyme having ability to oxidize cholesterol in the presence of an oxidized coenzyme and form a reduced coenzyme. Examples of such cholesterol dehydrogenase that can be used in the present invention include: a cholesterol dehydrogenase derived from animals, plants or microorganisms; and a cholesterol dehydrogenase, which is produced by genetic engineering methods. Commercially available products such as a cholesterol dehydrogenase (CHDH "Amano" 5; manufactured by Amano Enzyme Inc.) may also be used. Moreover, a combination of two or more cholesterol dehydrogenases can also be applied in the present invention. As such cholesterol dehydrogenase, either an unmodified enzyme or a chemically modified enzyme may be used. Such a chemically modified cholesterol dehydrogenase can be prepared, for example, by the above described chemical modification method using the above described chemically modifying reagent.

The concentration of the cholesterol dehydrogenase applied in the measurement method of the present invention is not particularly limited, as long as it is a concentration, at which the measurement of HDL3-C of the present invention can be carried out. The concentration of the cholesterol dehydrogenase in the reaction solution is generally 0.001 to 800 kU/L, and preferably 0.01 to 300 kU/L.

In the measurement method of the present invention using a cholesterol dehydrogenase, an oxidized coenzyme is used. Examples of such oxidized coenzyme include NAD, NADP, thio-NAD, and thio-NADP.

The concentration of an oxidized coenzyme in the measurement method of the present invention is not particularly limited, as long as it is a concentration at which the HDL3-C measurement of the present invention can be carried out. The concentration of the oxidized coenzyme in a reaction solution is generally from 0.01 to 400 mmol/L, and preferably from 0.1 to 100 mmol/L.

Examples of the reduced coenzyme of the present invention include NADH, NADPH, thio-NADH, and thio-NADPH.

The divalent metal salt used in the present invention is not particularly limited, as long as it can be used for the HDL3-C measurement of the present invention. Examples of the divalent metal salt include a magnesium salt, a calcium salt, and a manganese salt. Among them, a magnesium salt or a calcium salt is preferable. In addition, a hydrate of the divalent metal salt and the like can also be used in the present invention. The magnesium salt is not particularly limited, as long as it can be used for the HDL3-C measurement of the present invention. Examples of the magnesium salt include magnesium chloride, magnesium nitrate, and magnesium sulfate. The calcium salt is not particularly limited, as long as it can be used for the HDL3-C measurement of the present invention. Examples of the calcium salt include calcium chloride, calcium nitrate, and calcium sulfate.

The concentration of the divalent metal salt in a reaction solution is not particularly limited in the measurement method of the present invention, as long as it is a concentration at which the HDL3-C measurement of the present invention can be carried out. The concentration of the divalent metal salt in the reaction solution is generally from 12 to 20 mmol/L, and preferably from 13 to 19 mmol/L.

The alkali metal salt used in the measurement method of the present invention is an alkali metal salt selected from the group consisting of a sulfate, a nitrate, a carbonate, an acetate and a halide. Examples of the alkali metal salt include lithium sulfate, lithium nitrate, lithium carbonate, lithium acetate, lithium fluoride, lithium chloride, lithium bromide, lithium iodide, sodium sulfate, sodium nitrate, sodium carbonate, sodium acetate, sodium fluoride, sodium chloride, sodium bromide, sodium iodide, potassium sulfate, potassium nitrate, potassium carbonate, potassium acetate, potassium fluoride, potassium chloride, potassium bromide, and potassium iodide.

The concentration of the alkali metal salt selected from the group consisting of a sulfate, a nitrate, a carbonate, an acetate and a halide in a reaction solution is not particularly limited in the measurement method of the present invention, as long as it is a concentration at which the HDL3-C measurement of the present invention can be carried out. The concentration of the alkali metal salt in the reaction solution is generally from 5 to 21 mmol/L, and preferably from 6 to 18 mmol/L.

The dextran sulfate or a salt thereof used in the measurement method of the present invention is not particularly limited, as long as it can be used for the HDL3-C measurement of the present invention. Dextran sulfate or a salt thereof having a molecular weight of 40,000 to 500,000 is preferable. The salt of dextran sulfate is not particularly limited, as long as it can be used for the HDL3-C measurement of the present invention. An example of the salt is a sodium salt. The concentration of the dextran sulfate or a salt thereof in a reaction solution is not particularly limited in the measurement method of the present invention, as long as it is a concentration at which the HDL3-C measurement of the present invention can be carried out. It is generally from 0.75 to 2.6 g/L, and preferably from 1.0 to 2.3 g/L.

The aqueous medium used in the present invention is not particularly limited, as long as it is an aqueous medium, with which the method for measuring HDL3-C of the present invention can be carried out. Examples of such an aqueous medium include deionized water, distilled water, and a buffer solution. Of these, a buffer solution is preferable.

The pH used in the method for measuring HDL3-C of the present invention is not particularly limited, as long as it is a pH value, at which the method for measuring HDL3-C of the present invention can be carried out. It is pH 4 to 10, for example. In case a buffer solution is used as an aqueous medium, it is desired to use a buffer suitable for the determined pH. Examples of such a buffer used in a buffer solution include a tris(hydroxymethyl)aminomethane buffer, a phosphate buffer, a borate buffer, and a Good's buffer.

Examples of such a Good's buffer include 2-morpholinoethanesulfonic acid (MES), bis(2-hydroxyethyl)iminotris(hydroxymethyl)methane (Bis-Tris), N-(2-acetamide)iminodiacetic acid (ADA), piperazine-N,N'-bis(2-ethanesulfonic acid) (PIPES), N-(2-acetamide)-2-aminoethanesulfonic acid (ACES), 3-morpholino-2-hydroxypropanesulfonic acid (MOPSO), N,N-bis(2-hydroxyethyl)-2-aminoethanesulfonic acid (BES), 3-morpholinopropanesulfonic acid (MOPS), N-[Tris(hydroxymethyl)methyl]-2-aminoethanesulfonic acid (TES), 2-[4-(2-hydroxyethyl)-1-piperazinyl]ethanesulfonic acid (HEPES), 3-[N,N-bis(2-hydroxyethyl)amino]-2-hydroxypropanesulfonic acid (DIPSO), N-[Tris(hydroxymethyl)methyl]-2-hydroxy-3-aminopropanesulfonic acid (TAPSO), piperazine-N,N'-bis(2-hydroxypropanesulfonic acid) (POPSO), 3-[4-(2-hydroxyethyl)-1-piperazinyl]-2-hydroxypropanesulfonic acid (HEPPSO), 3-[4-(2-hydroxyethyl)-1-piperazinyl]propanesulfonic acid [(H)EPPS], N-[Tris(hydroxymethyl)methyl]glycine (Tricine), N,N-bis(2-hydroxyethyl)glycine (Bicine), N-Tris(hydroxymethyl)methyl-3-aminopropanesulfonic acid (TAPS), N-cyclohexyl-2-aminoethanesulfonic acid (CHES), N-cyclohexyl-3-amino-2-hydroxypropanesulfonic acid (CAPSO), and N-cyclohexyl-3-aminopropanesulfonic acid (CAPS).

The concentration of such a buffer solution is not particularly limited, as long as it is suitable for measurement. It is preferably 0.001 to 2.0 mol/L, and more preferably 0.005 to 1.0 mol/L.

The reaction temperature applied in the method for measuring HDL3-C of the present invention is not particularly limited, as long as it is a temperature, at which the method for measuring HDL3-C of the present invention can be carried out. It is preferably 10° C. to 50° C., and more preferably 30° C. to 40° C. The reaction temperature is generally set at 37° C. in a commonly used automatic analyzer.

The reaction time applied in the method for measuring HDL3-C of the present invention is not particularly limited, as long as it is a time, at which the method for measuring HDL3-C of the present invention can be carried out. It is preferably 1 to 60 minutes, and more preferably 2 to 30 minutes.

In case a combination of a cholesterol ester hydrolase and a cholesterol oxidase is used as cholesterol-measuring enzymes in the method for measuring HDL3-C of the present invention, the measurement of HDL3-C can be carried out by measuring the amount of hydrogen peroxide formed as a result of the reaction.

The amount of the formed hydrogen peroxide can be measured, for example, using a hydrogen peroxide electrode or a reagent for measuring hydrogen peroxide. The reagent for measuring hydrogen peroxide is a reagent for converting the formed hydrogen peroxide to a detectable substance. Such detectable substances include a dye and a luminescent substance. Of these, a dye is preferable. In case the detectable substance is a dye, the reagent for measuring hydrogen peroxide comprises an oxidative coloring chromogen and a peroxidative substance such as a peroxidase. Examples of such an oxidative coloring chromogen include the after-mentioned oxidative coloring chromogens. In case the detectable substance is a luminescent substance, the reagent for measuring hydrogen peroxide comprises a chemiluminescent substance. Examples of such a chemiluminescent substance include luminol, isoluminol, lucigenin, and acridinium ester.

In case a reagent comprising an oxidative coloring chromogen or a peroxidative substance such as peroxidase is used as a reagent for measuring hydrogen peroxide, hydrogen peroxide reacts with the oxidative coloring chromogen in the presence of the peroxidative substance to form a dye. Hence, the hydrogen peroxide can be measured by measuring the thus formed dye. On the other hand, in case a reagent for measuring hydrogen peroxide containing a chemiluminescent substance is used, hydrogen peroxide reacts with the chemiluminescent substance to generate a photon. Hence, the hydrogen peroxide can be measured by measuring the thus produced photon.

Examples of the oxidative coloring chromogen include a leuco-type chromogen and an oxidative coupling-coloring chromogen. The leuco-type chromogen is a substance that is converted to a dye by itself in the presence of hydrogen peroxide and a peroxidative substance such as peroxidase. Specific examples include tetramethylbenzidine, o-phenylenediamine, 10-N-carboxymethylcarbamoyl-3,7-bis(dimethylamino)-10H-phenothiazine (CCAP), 10-N-methylcarbamoyl-3,7-bis(dimethylamino)-10H-phenothiazine (MCDP), N-(carboxymethylaminocarbonyl)-4,4'-bis(dimethylamino)diphenylamine sodium salt (DA-64), 10-N-(carboxymethylaminocarbonyl)-3,7-bis(dimethylamino)-10H-phenothiazine sodium salt (DA-67), 4,4'-bis(dimethylamino)diphenylamine, and bis[3-bis(4-chlorophenyl)methyl-4-dimethylaminophenyl]amine (BCMA).

The oxidative coupling-coloring chromogen is a substance that forms a dye as a result of the oxidative coupling of two compounds in the presence of hydrogen peroxide and a peroxidative substance such as peroxidase. Examples of the combination of two compounds include a combination of a coupler and an aniline compound and a combination of a coupler and a phenol compound.

Examples of the coupler include 4-aminoantipyrine (4-AA) and 3-methyl-2-benzothiazolinonehydrazone.

Examples of the aniline compound include N-(3-sulfopropyl)aniline, N-ethyl-N-(2-hydroxy-3-sulfopropyl)-3-methylaniline (TOGS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-(3-sulfopropyl)-3-methylaniline (TOPS), N-(2-hydroxy-3-sulfopropyl)-3,5-dimethoxyaniline (HDAOS), N,N-dimethyl-3-methylaniline, N,N-di(3-sulfopropyl)-3,5-dimethoxyaniline, N-ethyl-N-(3-sulfopropyl)-3- methoxyaniline, N-ethyl-N-(3-sulfopropyl)aniline, N-ethyl-N-(3-sulfopropyl)-3,5-dimethoxyaniline, N-(3-sulfopropyl)-3,5-dimethoxyaniline, N-ethyl-N-(3-sulfopropyl)-3,5-dimethylaniline, N-ethyl-N-(2-hydroxy-3-sulfopropyl)-3-methoxyaniline, N-ethyl-N-(2-hydroxy-3-sulfopropyl)aniline, N-ethyl-N-(3-methylphenyl)-N'-succinylethylenediamine (EMSE), N-(3,5-dimethoxyphenyl)-N'-succinylethylenediamine (DOSE), N-ethyl-N-(3-methylphenyl)-N'-acetylethylenediamine, N-ethyl-N-(2-hydroxy-3-sulfopropyl)-4-fluoro-3,5-dimethoxyaniline (F-DAOS), N-[2-(succinylamino)ethyl]-2-methoxy-5-methylaniline (MASE), and N-ethyl-N-[2-(succinylamino)ethyl]-2-methoxy-5-methylaniline (Et-MASE).

Examples of the phenol compound include phenol, 4-chlorophenol, 3-methylphenol, and 3-hydroxy-2,6-triiodobenzoic acid (HTIB).

The concentration of the peroxidative substance in the measurement of hydrogen peroxide is not particularly limited, as long as it is a concentration suitable for the measurement. In case peroxidase is used as such a peroxidative substance, the concentration of the peroxidase is preferably 1 to 100 kU/L. Moreover, the concentration of an oxidative coloring chromogen is not particularly limited, as long as it is a concentration suitable for the measurement of hydrogen peroxide. It is preferably 0.01 to 10 g/L.

In case a combination of a cholesterol ester hydrolase, an oxidized coenzyme and a cholesterol dehydrogenase is used as cholesterol-measuring enzymes in the method for measuring HDL3-C of the present invention, the measurement of HDL3-C can be carried out by measuring the amount of a reduced coenzyme formed as a result of the reaction.

The amount of the formed reduced coenzyme can be measured, for example, by absorptiometry or using a reagent for measuring a reduced coenzyme. Examples of the absorptiometry include the above-mentioned absorptiometry. The reagent for measuring a reduced coenzyme is a reagent for converting the formed reduced coenzyme to a detectable substance. Examples of such a detectable substance include a dye.

Examples of the reagent for measuring a reduced coenzyme include a reagent comprising a diaphorase, an electron carrier and a reductive coloring chromogen, a reagent comprising a reduced coenzyme oxidase, and a reagent comprising a reduced coenzyme oxidase and a reagent for measuring hydrogen peroxide.

In case a reagent comprising diaphorase, an electronic carrier and a reductive coloring chromogen is used as a reagent for measuring a reduced coenzyme, a reduced coenzyme can be quantitatively determined by quantifying a dye formed as a result of the conversion of the reductive coloring chromogen. Examples of the electronic carrier include 1-methoxy-5-methylphenazium methylsulfate.

Examples of the reductive coloring chromogen include 3-(4,5-dimethyl-2-thiazolyl)-2,5-diphenyl-2H-tetrazolium bromide (MTT), 2-(4-iodophenyl)-3-(4-nitrophenyl)-5-(2,4-disulfophenyl)-2H-tetrazolium monosodium salt (WST-1), and 2-(4-iodophenyl)-3-(2,4-dinitrophenyl)-5-(2,4-disulfophenyl)-2H-tetrazolium monosodium salt (WST-3).

In case the reagent comprising a reduced coenzyme oxidase is used as a reagent for measuring a reduced coenzyme, the reduced coenzyme can be measured by measuring hydrogen peroxide formed as a result of the reaction of a reductive coloring chromogen and the reduced coenzyme oxidase. The formed hydrogen peroxide can be measured, for example, by a method using the above described hydrogen peroxide electrode, or by a method using the above described reagent for measuring hydrogen peroxide. In case the reduced coenzyme is measured by the method using the reagent for measuring hydrogen peroxide, the reagent for measuring a reduced coenzyme comprises a reduced coenzyme oxidase and a reagent for measuring hydrogen peroxide.

<Method for Measuring Cholesterol in HDL2>

HDL is a lipoprotein consisting of two subfractions, namely, HDL2 and HDL3. Thus, the concentration of HDL2 cholesterol (hereinafter referred to as HDL2-C) in a sample can be measured by measuring HDL cholesterol (total HDL cholesterol) in the sample, and then subtracting, from the concentration of the total HDL cholesterol, the concentration of HDL3-C in the sample measured by the method for measuring HDL3-C of the present invention.

Specifically, the method for measuring HDL2-C in a sample of the present invention comprises the following steps:

(1) a step of measuring cholesterol in HDL contained in a sample;
(2) a step of measuring HDL3-C in the sample by the method for measuring HDL3-C of the present invention; and
(3) a step of subtracting the measurement value obtained by the measurement in the step (2) from the measurement value obtained by the measurement in the step (1).

The measurement of cholesterol in HDL (hereinafter referred to as HDL-C) in the step (1) is not particularly limited, as long as it is a method capable of measuring cholesterol in total HDL contained in a sample. The measurement can be carried out by, for example, the methods described in Japanese unexamined Patent Application Publication No. 8-131197, International Publication WO2004/035816, International Publication WO2006/118199, etc. In addition, the measurement of HDL-C can also be carried out using commercially available reagents for measuring HDL-C and commercially available kits for measuring HDL-C. Examples of such a commercially available reagent for measuring HDL-C and a commercially available kit for measuring HDL-C include "MetaboLead HDL-C" (manufactured by Kyowa Medex Co., Ltd.) and "Determiner HDL-C" (manufactured by Kyowa Medex Co., Ltd.).

The measurement of HDL3-C in the step (2) can be carried out by the above described method for measuring HDL3-C.

<Reagent for Measuring HDL3-C>

The reagent for measuring HDL3-C of the present invention is used for the method for measuring HDL3-C of the present invention.

The embodiments of the reagent for measuring HDL3-C of the present invention are described below.

Measuring Reagent 1

A reagent comprising a cholesterol ester hydrolase, a cholesterol oxidase, (a) a divalent metal salt, (b) an alkali metal salt selected from the group consisting of a sulfate, a nitrate, a carbonate, an acetate and a halide, and (c) dextran sulfate or a salt thereof Measuring Reagent 2

A reagent comprising a cholesterol ester hydrolase, a cholesterol oxidase, (a) a divalent metal salt, (b) an alkali metal salt selected from the group consisting of a sulfate, a nitrate, a carbonate, an acetate and a halide, (c) dextran sulfate or a salt thereof, and a reagent for measuring hydrogen peroxide Measuring Reagent 3

A reagent comprising a cholesterol ester hydrolase, an oxidized coenzyme, a cholesterol dehydrogenase, (a) a divalent metal salt, (b) an alkali metal salt selected from the group consisting of a sulfate, a nitrate, a carbonate, an acetate and a halide, and (c) dextran sulfate or a salt thereof Measuring Reagent 4

A reagent comprising a cholesterol ester hydrolase, an oxidized coenzyme, a cholesterol dehydrogenase, (a) a divalent metal salt, (b) an alkali metal salt selected from the group consisting of a sulfate, a nitrate, a carbonate, an acetate and a halide, (c) dextran sulfate or a salt thereof, and a reagent for measuring a reduced coenzyme The reagent for measuring HDL3-C of the present invention may be either in a freeze-dried state or in a state dissolved in an aqueous medium. In case HDL3-C contained in a sample is measured using such a freeze-dried reagent, the reagent is dissolved in an aqueous medium before use.

In case the reagent for measuring HDL3-C of the present invention is in a state being dissolved in an aqueous medium, the concentration of each component in the reagent is not particularly limited, as long as it is a concentration at which the HDL3-C measurement of the present invention can be carried out. For example, the concentrations of individual elements in a reaction solution are as follows.

Cholesterol ester hydrolase: generally 0.001 to 800 kU/L, and preferably 0.01 to 300 kU/L.

Cholesterol oxidase: generally 0.001 to 800 kU/L, and preferably 0.01 to 300 kU/L.

Cholesterol dehydrogenase: generally 0.001 to 800 kU/L, and preferably 0.01 to 300 kU/L.

Oxidized coenzyme: generally 0.01 to 400 mmol/L, and preferably 0.1 to 100 mmol/L.

Divalent metal salt: generally 12 to 20 mmol/L, and preferably 13 to 19 mmol/L.

Alkali metal salt selected from the group consisting of a sulfate, a nitrate, a carbonate, an acetate and a halide: generally 5 to 21 mmol/L, and preferably 6 to 18 mmol/L.

Dextran sulfate or a salt thereof: generally 0.75 to 2.6 g/L, and preferably 1.0 to 2.3 g/L.

In case the reagent for measuring HDL3-C of the present invention is in a freeze-dried state, the content of each component in the reagent is not particularly limited, as long as it is a content at which the HDL3-C measurement of the present invention can be carried out. For example, it may be such a content that the concentration of each component in a reaction solution can be the above described concentration.

The content of each component in the reagent for measuring HDL3-C of the present invention is such a content that the concentration of each component in a state of being dissolved in an aqueous medium can be, for example, as follows.

Cholesterol ester hydrolase: generally 0.001 to 800 kU/L, and preferably 0.01 to 300 kU/L.

Cholesterol oxidase: generally 0.001 to 800 kU/L, and preferably 0.01 to 300 kU/L.

Cholesterol dehydrogenase: generally 0.001 to 800 kU/L, and preferably 0.01 to 300 kU/L.

Oxidized coenzyme: generally 0.01 to 400 mmol/L, and preferably 0.1 to 100 mmol/L.

Divalent metal salt: generally 12 to 20 mmol/L, and preferably 13 to 19 mmol/L.

Alkali metal salt selected from the group consisting of a sulfate, a nitrate, a carbonate, an acetate and a halide: generally 5 to 21 mmol/L, and preferably 6 to 18 mmol/L.

Dextran sulfate or a salt thereof: generally 0.75 to 2.6 g/L, and preferably 1.0 to 2.3 g/L.

<Kit for Measuring HDL3-C>

The reagent for measuring HDL3-C of the present invention is used for the method for measuring HDL3-C of the present invention and can take the form of a kit, suitable for preservation, distribution and use. Examples of the kit for measuring HDL3-C of the present invention include a two-reagent system kit and a three-reagent system kit. Of these, the two-reagent system kit consisting of a first reagent and a second reagent is preferable.

In such a two-reagent system kit for measuring HDL3-C consisting of a first reagent and a second reagent, a cholesterol ester hydrolase is comprised in either the first reagent or the second reagent, or in both of the first and second reagents. A cholesterol oxidase is preferably comprised in the second reagent. An oxidized coenzyme is comprised in either the first reagent or the second reagent, or in both of the first and second reagents. A cholesterol dehydrogenase is preferably comprised in the second reagent. A divalent metal salt is preferably comprised in the first reagent. An alkali metal salt selected from the group consisting of a sulfate, a nitrate, a carbonate, an acetate and a halide is preferably comprised in the first reagent. Dextran sulfate or a salt thereof is preferably comprised in the first reagent.

A reagent for measuring hydrogen peroxide may be contained in either the first reagent or the second reagent, or in both of the first and second reagents. In case this reagent comprises oxidative coupling chromogens, two compounds of oxidative coupling chromogens, namely, a coupler and an aniline, or a coupler and a phenol are preferably each comprised in different reagents, separately.

A reagent for measuring a reduced coenzyme is comprised in either the first reagent or the second reagent, or in both of the first and second reagents.

The embodiments of the kit for measuring HDL3-C of the present invention are described below.

Measuring Kit 1
First Reagent

A reagent comprising (a) a divalent metal salt, (b) an alkali metal salt selected from the group consisting of a sulfate, a nitrate, a carbonate, an acetate and a halide, and (c) dextran sulfate or a salt thereof.

Second Reagent

A reagent comprising a cholesterol ester hydrolase and a cholesterol oxidase

Measuring Kit 2
First Reagent

A reagent comprising (a) a divalent metal salt, (b) an alkali metal salt selected from the group consisting of a sulfate, a nitrate, a carbonate, an acetate and a halide, (c) dextran sulfate or a salt thereof, and a reagent for measuring hydrogen peroxide Second Reagent A reagent comprising a cholesterol ester hydrolase, a cholesterol oxidase, and a reagent for measuring hydrogen peroxide Measuring Kit 3
First Reagent A reagent comprising (a) a divalent metal salt, (b) an alkali metal salt selected from the group consisting of a sulfate, a nitrate, a carbonate, an acetate and a halide, and (c) dextran sulfate or a salt thereof.

Second Reagent

A reagent comprising a cholesterol ester hydrolase, an oxidized coenzyme, and a cholesterol dehydrogenase Measuring kit 4
First Reagent A reagent comprising (a) a divalent metal salt, (b) an alkali metal salt selected from the group consisting of a sulfate, a nitrate, a carbonate, an acetate and a halide, (c) dextran sulfate or a salt thereof, and a reagent for measuring a reduced coenzyme Second Reagent A reagent comprising a cholesterol ester hydrolase, an oxidized coenzyme, a cholesterol dehydrogenase, and a reagent for measuring a reduced coenzyme The kit for measuring HDL3-C of the present invention may be either in a freeze-dried state or a state dissolved in an aqueous medium. In case HDL3-C contained in a sample is measured using such a freeze-dried kit, the freeze-dried reagents of the kit are dissolved in an aqueous medium before use. Examples of the aqueous medium include the aforementioned aqueous media.

In case the kit for measuring HDL3-C of the present invention is in a state dissolved in an aqueous medium, the concentration of each component in the first or second reagent of the kit is not particularly limited, as long as it is a concentration at which the HDL3-C measurement of the present invention can be carried out. For example, the concentration of each component in a reaction solution are as follows.

Cholesterol ester hydrolase (in the first reagent or the second reagent): generally 0.001 to 800 kU/L, and preferably 0.01 to 300 kU/L.

Cholesterol oxidase (in the second reagent): generally 0.001 to 800 kU/L, and preferably 0.01 to 300 kU/L.

Cholesterol dehydrogenase (in the second reagent): generally 0.001 to 800 kU/L, and preferably 0.01 to 300 kU/L.

Oxidized coenzyme (in the first reagent or the second reagent): generally 0.01 to 400 mmol/L, and preferably 0.1 to 100 mmol/L.

Divalent metal salt (in the first reagent): generally 12 to 20 mmol/L, and preferably 13 to 19 mmol/L.

Alkali metal salt selected from the group consisting of a sulfate, a nitrate, a carbonate, an acetate and a halide (in the first reagent): generally 5 to 21 mmol/L, and preferably 6 to 18 mmol/L.

Dextran sulfate or a salt thereof (in the first reagent): generally 0.75 to 2.6 g/L, and preferably 1.0 to 2.3 g/L.

In case the kit for measuring HDL3-C of the present invention is in a freeze-dried state, the content of each component in the first or second reagent of the kit is not particularly limited, as long as it is a content at which the HDL3-C measurement of the present invention can be carried out. For example, it may be such a content that the concentration of each component in a reaction solution can be the aforementioned concentration.

The content of each component in the first or second reagent of the kit for measuring HDL3-C of the present invention is such a content that the concentration of each component in a state of being dissolved in an aqueous medium can be, for example, as follows.

Cholesterol ester hydrolase (in the first reagent or the second reagent): generally 0.001 to 800 kU/L, and preferably 0.01 to 300 kU/L.

Cholesterol oxidase (in the second reagent): generally 0.001 to 800 kU/L, and preferably 0.01 to 300 kU/L.

Cholesterol dehydrogenase (in the second reagent): generally 0.001 to 800 kU/L, and preferably 0.01 to 300 kU/L.

Oxidized coenzyme (in the first reagent or the second reagent): generally 0.01 to 400 mmol/L, and preferably 0.1 to 100 mmol/L.

Divalent metal salt (in the first reagent): generally 16 to 27 mmol/L, and preferably 17 to 25 mmol/L.

Alkali metal salt selected from the group consisting of a sulfate, a nitrate, a carbonate, an acetate and a halide (in the first reagent): generally 7 to 28 mmol/L, and preferably 8 to 25 mmol/L.

Dextran sulfate or a salt thereof (in the first reagent): generally 1.0 to 3.5 g/L, and preferably 1.3 to 3.1 g/L.

The reagent for measuring HDL3-C and kit for measuring HDL3-C of the present invention may also comprise an aqueous medium, a stabilizer, an antiseptic agent, an interference inhibitor, a reaction promoter and the like, as necessary. Examples of the aqueous medium include the aforementioned aqueous media. Examples of the stabilizer include ethylenediaminetetraacetic acid (EDTA), sucrose, calcium chloride, and cholic acid or a salt thereof. Examples of the antiseptic agent include sodium azide and an antibiotic. An example of the interference inhibitor is ascorbic acid oxidase used to remove the influence of ascorbic acid. Examples of the reaction promoter include colipase and phospholipase.

In the reagent for measuring HDL3-C and kit for measuring HDL3-C of the present invention, the aforementioned cholesterol ester hydrolase, cholesterol oxidase, oxidized coenzyme, cholesterol dehydrogenase, divalent metal salt, alkali metal salt (an alkali metal salt selected from the group consisting of a sulfate, a nitrate, a carbonate, an acetate and a halide), dextran sulfate or a salt thereof, a reagent for measuring hydrogen peroxide, and a reagent for measuring a reduced coenzyme can be used.

<Kit for Measuring HDL2-C>

The HDL2-C-measuring kit of the present invention is used for the method for measuring HDL2-C of the present invention. Examples of the kit for measuring HDL2-C of the present invention include: a kit comprising the reagent for measuring HDL3-C of the present invention and a reagent for measuring HDL-C; and a kit comprising the first and second reagents of the kit for measuring HDL3-C of the present invention, and a reagent for measuring HDL-C. The reagent for measuring HDL3-C of the present invention used in the kit for measuring HDL2-C of the present invention may be the kit for measuring HDL3-C of the present invention.

The reagent for measuring HDL-C used in the kit for measuring HDL2-C of the present invention may be in a form of an HDL-C-measuring kit. The reagent for measuring HDL-C and the HDL-C-measuring kit are not particularly limited, as long as they are a reagent and a kit, which are capable of measuring HDL-C. For example, the reagents and kits for measuring HDL-C described in Japanese unexamined Patent Application Publication No. 8-131197, International Publication WO2004/035816, and International Publication WO2006/118199 can be used. Moreover, as such a reagent and a kit for measuring HDL-C, commercially available reagents and kits for measuring HDL-C can also be used. As such a commercially available reagent and a commercially available kit for measuring HDL-C, the aforementioned commercially available reagent and the aforementioned commercially available kit for measuring HDL-C can be used.

Hereinafter, the present invention will be described more in detail in the following examples. However, these examples are not intended to limit the scope of the present invention. In the present examples and comparative examples, the reagents and enzymes manufactured by the following manufacturers were used:

HEPES (manufactured by VWR), HSDA (manufactured by Dojindo Laboratories), PIPES (manufactured by Dojindo Laboratories), sodium cholate (manufactured by Acros), bovine serum albumin (BSA; manufactured by Celliance), 4-aminoantipyrine (manufactured by Saikyo Kasei), dextran sulfate sodium with a molecular weight of 500,000 (manufactured by Meito Sangyo Co., Ltd.), dextran sulfate sodium with a molecular weight of 40,000 (manufactured by ICN), magnesium nitrate hexahydrate (manufactured by Kanto Chemical Co., Inc.), calcium chloride dihydrate (manufactured by Wako Pure Chemical Industries, Ltd.), sodium sulfate (manufactured by Kanto Chemical Co., Inc.), sodium chloride (manufactured by Wako Pure Chemical Industries, Ltd.), potassium chloride (manufactured by Wako Pure Chemical Industries, Ltd.), lithium chloride (manufactured by Wako Pure Chemical Industries, Ltd.), sodium nitrate (manufactured by Nacalai Tesque Inc.), sodium carbonate (manufactured by Kanto Chemical Co., Inc.), sodium bromide (manufactured by Wako Pure Chemical Industries, Ltd.), sodium acetate trihydrate (manufactured by Kanto Chemical Co., Inc.), sodium fluoride (manufactured by Wako Pure Chemical Industries, Ltd.), COO322 (cholesterol oxidase; manufactured by Toyobo Co., Ltd.), LPL311 (cholesterol ester hydrolase; manufactured by Toyobo Co., Ltd.), and peroxidase (manufactured by Toyobo Co., Ltd.)

Moreover, chemically modified LPL311 was prepared as follows and was then used.

LPL311 was added to a HEPES buffer (pH 8.5, 0.15 mol/L) to a concentration of 33 g/L, and the obtained solution was then cooled to 5° C. Thereafter, SUNBRIGHT VFM-4101 (manufactured by NOF Corporation) was added to the resulting solution to a concentration of 330 g/L, and the obtained mixture was further reacted for 3 hours. The obtained modified enzyme solution was as such used as chemically modified LPL311 without purification and separation.

Chemically modified COO322 was prepared as follows and was then used.

COO322 was added to a HEPES buffer (pH 8.0, 0.1 mol/L) to a concentration of 50 g/L, and the obtained solution was then cooled to 15° C. Thereafter, SUNBRIGHT VFM-4101 (manufactured by NOF Corporation) was added to the resulting solution to a concentration of 6.25 g/L, and the obtained mixture was further reacted for 2 hours. The obtained modified enzyme solution was as such used as chemically modified COO322 without purification and separation.

EXAMPLE 1

Measurement of HDL3-C by Combination of Divalent Metal Salt and Sodium Sulfate A kit for measuring HDL3-C consisting of the following first reagent and second reagent was prepared. The prepared kits each comprising a divalent metal salt (magnesium nitrate hexahydrate or calcium chloride dihydrate) and sodium sulfate, which had such concentrations as shown in Table 1, were defined as kits of Examples 1(1) to 1(11).

First Reagent

| HEPES (pH 7.0) | 10 mmol/L |
| HSDA | 0.3 g/L |
| Sodium cholate | 0.75 g/L |
| Peroxidase | 10 kU/L |
| Dextran sulfate sodium | x g/L (see Table 1) |
| Divalent metal salt | y mmol/L (see Table 1) |
| Sodium sulfate | z mmol/L (see Table 1) |

Second Reagent

| PIPES (pH 7.0) | 10 mmol/L |
| 4-Aminoantipyrine | 0.3 g/L |
| Sodium cholate | 6 g/L |
| Peroxidase | 20 kU/L |
| Chemically modified LPL311 | 0.2 kU/L |
| Chemically modified COO322 | 7.6 kU/L |

Comparative Example 1

A kit for measuring HDL3-C consisting of the following first reagent and second reagent was prepared. The prepared kits each comprising magnesium nitrate hexahydrate having such concentrations as shown in Table 1, were defined as kits of Comparative Examples 1(1) to 1(3).

First Reagent

| HEPES (pH 7.0) | 10 mmol/L |
| HSDA | 0.3 g/L |
| Sodium cholate | 0.75 g/L |
| Peroxidase | 10 kU/L |
| Dextran sulfate sodium | x g/L (see Table 1) |
| Magnesium nitrate hexahydrate | y mmol/L (see Table 1) |

Second Reagent

| PIPES (pH 7.0) | 10 mmol/L |
| 4-Aminoantipyrine | 0.3 g/L |
| Sodium cholate | 6 g/L |
| Peroxidase | 20 kU/L |
| Chemically modified LPL311 | 0.2 kU/L |
| Chemically modified CHOD322 | 7.6 kU/L |

EXAMPLE 2

Using the kit of Example 1(a), HDL3-C contained in each of 42 human serum samples, in which the triglyceride level was 200 mg/dL or less, was measured as follows. Thereafter, a correlation coefficient with a fractionation method was calculated.

(1) Calculation of "Reaction Absorbance" in Human Serum Sample as a Result of Reaction of the Sample with Kit of Example 1 (a)

Using Hitachi 7170S Auto Analyzer, the "reaction absorbance" was calculated by the following operations.

Human serum (2 µL) used as a sample was added to a reaction cell, and the first reagent (0.15 mL) of the kit of Example 1(a) was then added thereto to initiate a reaction (first reaction). The aforementioned mixture was incubated at 37° C. for 5 minutes, and the absorbance (E1) of the reaction solution obtained 5 minutes after initiation of the reaction was then measured at a dominant wavelength of 600 nm and a sub-wavelength of 700 nm. Subsequently, the second reagent (0.05 mL) of the kit of Example 1(a) was added to the reaction solution, and the obtained mixture was then incubated at 37° C. for 5 minutes for a reaction (second reaction). The absorbance (E2) of the reaction solution obtained 5 minutes after initiation of the second reaction was measured at a dominant wavelength of 600 nm and a sub-wavelength of 700 nm. Thereafter, E1 was subtracted from E2 to calculate a change in absorbance ($\Delta E_{serum}$ sample). Moreover, a normal saline was used as a sample, instead of human serum, and the same measurement as described above was carried out to calculate a change in absorbance ($\Delta E_{blank}$). Finally, according to the following (formula 1), the "reaction absorbance" in each human serum sample was calculated.

[Expression 1]

$$\text{Reaction absorbance} = \Delta E_{serum\ sample} - \Delta E_{blank} \quad \text{(Formula 1)}$$

(2) Measurement of HDL3-C Contained in Human Serum Sample by a Fractionation Method Using the same human serum sample as used in (1) above, HDL3 was separated from each sample by the method described in Journal of Lipid Research vol. 49, p. 1130-1136 (2008) (fractionation method), and the amount of cholesterol in the obtained HDL3 fraction was measured using Determiner L TCII (manufactured by Kyowa Medex Co., Ltd.).

In addition, as a reference, using the same human serum sample as mentioned above, HDL was separated from each sample by DCM (Designated Comparison Method) described in Clinical Chemistry, Vol. 45, No. 10, pp. 1803-1812 (1999), and the amount of cholesterol in the obtained HDL fraction was measured using Determiner L TCII (manufactured by Kyowa Medex Co., Ltd.).

(3) Correlation Between the Measurement Method of the Present Invention and Fractionation Method The correlation coefficient between the "reaction absorbance" in the measurement using the kit of Example 1(1) and the measurement value obtained by the fractionation method described in (2) is shown in Table 1.

Likewise, each of the kits of Examples 1(2) to 1(11) was used instead of the kit of Example 1(1), and the correlation coefficient between the reaction absorbance in the measurement using each of the kits and the measurement value obtained by the fractionation method was determined. The correlation is shown in Table 1.

Comparative Example 2

The correlation coefficient between the "reaction absorbance" in the measurement using the kit of each of Comparative Examples 1(1) to 1(3) and the measurement value obtained by the fractionation method was determined by the same method as that applied in Example 2 with the exception that each of the kits of Comparative Examples 1(1) to 1(3) was used instead of the kit of Example 1(1). The determined correlation coefficients are shown in Table 1.

From the results shown in Table 1, it proved that a good correlation was not observed between the measurement using each of the kits of Comparative Examples 1(1) to 1(3) comprising no sodium sulfate as an alkali metal salt in the first reagent, and the measurement of HDL3-C by the fractionation method, and that a good correlation was rather observed between the measurement using each of the kits of Comparative Examples 1(1) to 1(3) and the measurement of HDL-C.

On the other hand, it proved that a good correlation was observed between the measurement using each of the kits of Examples 1(1) to 1(11) comprising sodium sulfate and a divalent metal salt in the first reagent, and the measurement of HDL3-C by the fractionation method.

EXAMPLE 3

Studies Regarding Magnesium Salt Concentration and Sodium Sulfate Concentration

A kit for measuring HDL3-C consisting of the following first reagent and second reagent was prepared. The prepared kits comprising magnesium nitrate hexahydrate and sodium sulfate having such concentrations as shown in Table 2, respectively, were defined as kits of Examples 3(1) to 3(12).

First Reagent

| | |
|---|---|
| HEPES (pH 7.0) | 10 mmol/L |
| HSDA | 0.3 g/L |
| Sodium cholate | 0.75 g/L |

TABLE 1

| Kit Measurement method | DexS•Na (Dextran sulfate sodium) | x (g/L) | Divalent metal salt | y (mmol/L) | $Na_2SO_4$ z (mmol/L) | Correlation coefficient (with respect to HDL3-C fractionation method) | Correlation coefficient (with respect to HDL-C measurement method) |
|---|---|---|---|---|---|---|---|
| Example 1 (1) Example 2 (1) | DexS•Na (Molecular weight: 500,000) | 2 | $Mg(NO_3)_2 \cdot 6H_2O$ | 20 | 7 | 0.827 | 0.363 |
| Example 1 (2) Example 2 (2) | DexS•Na (Molecular weight: 500,000) | 2 | $Mg(NO_3)_2 \cdot 6H_2O$ | 25 | 7 | 0.800 | 0.162 |
| Example 1 (3) Example 2 (3) | DexS•Na (Molecular weight: 500,000) | 2 | $Mg(NO_3)_2 \cdot 6H_2O$ | 16 | 3.5 | 0.863 | — |
| Example 1 (4) Example 2 (4) | DexS•Na (Molecular weight: 500,000) | 2 | $Mg(NO_3)_2 \cdot 6H_2O$ | 16 | 7 | 0.721 | — |
| Example 1 (5) Example 2 (5) | DexS•Na (Molecular weight: 500,000) | 2 | $CaCl_2 \cdot 2H_2O$ | 16 | 3.5 | 0.775 | — |
| Example 1 (6) Example 2 (6) | DexS•Na (Molecular weight: 500,000) | 2 | $CaCl_2 \cdot 2H_2O$ | 16 | 7 | 0.853 | — |
| Example 1 (7) Example 2 (7) | DexS•Na (Molecular weight: 500,000) | 1 | $Mg(NO_3)_2 \cdot 6H_2O$ | 23 | 7 | 0.849 | — |
| Example 1 (8) Example 2 (8) | DexS•Na (Molecular weight: 500,000) | 1.5 | $Mg(NO_3)_2 \cdot 6H_2O$ | 23 | 7 | 0.874 | — |
| Example 1 (9) Example 2 (9) | DexS•Na (Molecular weight: 500,000) | 2 | $Mg(NO_3)_2 \cdot 6H_2O$ | 23 | 7 | 0.870 | — |
| Example 1 (10) Example 2 (10) | DexS•Na (Molecular weight: 500,000) | 3.5 | $Mg(NO_3)_2 \cdot 6H_2O$ | 23 | 7 | 0.877 | — |
| Example 1 (11) Example 2 (11) | DexS•Na (Molecular weight: 40,000) | 1.5 | $Mg(NO_3)_2 \cdot 6H_2O$ | 23 | 7 | 0.906 | — |
| Comparative Example 1 (1) Comparative Example 2 (1) | DexS•Na (Molecular weight: 500,000) | 2 | $Mg(NO_3)_2 \cdot 6H_2O$ | 4 | 0 | 0.414 | 0.934 |
| Comparative Example 1 (2) Comparative Example 2 (2) | DexS•Na (Molecular weight: 500,000) | 2 | $Mg(NO_3)_2 \cdot 6H_2O$ | 7 | 0 | 0.414 | 0.966 |
| Comparative Example 1 (3) Comparative Example 2 (3) | DexS•Na (Molecular weight: 500,000) | 2 | $Mg(NO_3)_2 \cdot 6H_2O$ | 10 | 0 | 0.590 | 0.867 |

-continued

| Peroxidase | 10 kU/L |
| Dextran sulfate sodium (molecular weight: 500,000) | 2 g/L |
| Magnesium nitrate hexahydrate | x mmol/L (see Table 2) |
| Sodium sulfate | y mmol/L (see Table 2) |

Second Reagent

| PIPES (pH 7.0) | 10 mmol/L |
| 4-Aminoantipyrine | 0.3 g/L |
| Sodium cholate | 6 g/L |
| Peroxidase | 20 kU/L |
| Chemically modified LPL311 | 0.2 kU/L |
| Chemically modified COO322 | 7.6 kU/L |

EXAMPLE 4

The correlation coefficient between the reaction absorbance in the measurement using each of the kits of Examples 3(1) to 3(12) and the measurement value obtained by the fractionation method was determined by the same method as that applied in Example 2 with the exception that each of the kits of Examples 3(1) to 3(12) was used instead of the kit of Example 1(1). The determined correlation coefficients are shown in Table 2.

TABLE 2

| Kit | Measurement method | $Mg(NO_3)_2 \cdot 6H_2O$ x (mmol/L) | $Na_2SO_4$ y (mmol/L) | Correlation coefficient (with respect to HDL3-C fractionation method) |
|---|---|---|---|---|
| Example 3 (1) | Example 4 (1) | 16 | 3.5 | 0.848 |
| Example 3 (2) | Example 4 (2) | 20 | 3.5 | 0.827 |
| Example 3 (3) | Example 4 (3) | 23 | 3.5 | 0.775 |
| Example 3 (4) | Example 4 (4) | 27 | 3.5 | 0.715 |
| Example 3 (5) | Example 4 (5) | 16 | 7 | 0.835 |
| Example 3 (6) | Example 4 (6) | 20 | 7 | 0.914 |
| Example 3 (7) | Example 4 (7) | 23 | 7 | 0.869 |
| Example 3 (8) | Example 4 (8) | 27 | 7 | 0.776 |
| Example 3 (9) | Example 4 (9) | 16 | 14 | 0.722 |
| Example 3 (10) | Example 4 (10) | 20 | 14 | 0.770 |
| Example 3 (11) | Example 4 (11) | 23 | 14 | 0.897 |
| Example 3 (12) | Example 4 (12) | 27 | 14 | 0.909 |

From the results shown in Table 2, it proved that a good correlation was observed between the measurement using each of the kits of Examples 3(1) to 3(12) comprising a magnesium salt and sodium sulfate in the first reagent, and the measurement of HDL3-C by the fractionation method.

EXAMPLE 5

Studies Regarding Alkali Metal Salt

A kit for measuring HDL3-C consisting of the following first reagent and second reagent was prepared. The prepared kits comprising alkali metal salts having such concentrations as shown in Table 3, respectively, were defined as kits of Examples 5(1a) to 5(9c).

First Reagent

| HEPES (pH 7.0) | 10 mmol/L |
| HSDA | 0.3 g/L |
| Sodium cholate | 0.75 g/L |
| Peroxidase | 10 kU/L |
| Dextran sulfate sodium (molecular weight: 500,000) | 2 g/L |
| Magnesium nitrate hexahydrate | 20 mmol/L |
| Alkali metal salt (see Table 3) | |

Second Reagent

| PIPES (pH 7.0) | 10 mmol/L |
| 4-Aminoantipyrine | 0.3 g/L |
| Sodium cholate | 6 g/L |
| Peroxidase | 20 kU/L |
| Chemically modified LPL311 | 0.2 kU/L |
| Chemically modified COO322 | 7.6 kU/L |

EXAMPLE 6

The correlation coefficient between the reaction absorbance in the measurement using each of the kits of Examples 5(1a) to 5(9c) and the measurement value obtained by the fractionation method was determined by the same method as that applied in Example 2 with the exception that each of the kits of Examples 5(1a) to 5(9c) was used instead of the kit of Example 1(1). The determined correlation coefficients are shown in Table 3.

TABLE 3

| Kit | Measurement method | Alkali metal salt Type of alkali metal salt | Concentration (mmol/L) | Correlation coefficient (with respect to HDL3-C fractionation method) |
|---|---|---|---|---|
| Example 5 (1a) | Example 6 (1a) | Sodium chloride (NaCl) | 7 | 0.918 |
| Example 5 (1b) | Example 6 (1b) | | 14 | 0.929 |
| Example 5 (1c) | Example 6 (1c) | | 28 | 0.917 |

TABLE 3-continued

| Kit | Measurement method | Alkali metal salt Type of alkali metal salt | Concentration (mmol/L) | Correlation coefficient (with respect to HDL3-C fractionation method) |
|---|---|---|---|---|
| Example 5 (2a) | Example 6 (2a) | Potassium chloride (KCl) | 7 | 0.929 |
| Example 5 (2b) | Example 6 (2b) | | 14 | 0.902 |
| Example 5 (2c) | Example 6 (2c) | | 28 | 0.744 |
| Example 5 (3a) | Example 6 (3a) | Lithium chloride (LiCl) | 7 | 0.905 |
| Example 5 (3b) | Example 6 (3b) | | 14 | 0.891 |
| Example 5 (3c) | Example 6 (3c) | | 28 | 0.920 |
| Example 5 (4a) | Example 6 (4a) | Sodium nitrate ($NaNO_3$) | 7 | 0.905 |
| Example 5 (4b) | Example 6 (4b) | | 14 | 0.929 |
| Example 5 (4c) | Example 6 (4c) | | 28 | 0.898 |
| Example 5 (5a) | Example 6 (5a) | Sodium carbonate | 3.5 | 0.935 |
| Example 5 (5b) | Example 6 (5b) | ($Na_2CO_3$) | 7 | 0.927 |
| Example 5 (5c) | Example 6 (5c) | | 14 | 0.776 |
| Example 5 (6a) | Example 6 (6a) | Sodium bromide (NaBr) | 7 | 0.898 |
| Example 5 (6b) | Example 6 (6b) | | 14 | 0.919 |
| Example 5 (6c) | Example 6 (6c) | | 28 | 0.894 |
| Example 5 (7a) | Example 6 (7a) | Sodium acetate trihydrate | 7 | 0.929 |
| Example 5 (7b) | Example 6 (7b) | ($CH_3CO_2Na \cdot 3H_2O$) | 14 | 0.932 |
| Example 5 (7c) | Example 6 (7c) | | 28 | 0.878 |
| Example 5 (8a) | Example 6 (8a) | Sodium fluoride (NaF) | 7 | 0.926 |
| Example 5 (8b) | Example 6 (8b) | | 14 | 0.891 |
| Example 5 (8c) | Example 6 (8c) | | 28 | 0.721 |
| Example 5 (9a) | Example 6 (9a) | Sodium sulfate ($Na_2SO_4$) | 3.5 | 0.827 |
| Example 5 (9b) | Example 6 (9b) | | 7 | 0.914 |
| Example 5 (9c) | Example 6 (9c) | | 14 | 0.770 |

From the results shown in Table 3, it proved that a good correlation was observed between the measurement using the kit comprising an alkali metal salt selected from the group consisting of a sulfate, a nitrate, a carbonate, an acetate and a halide in the first reagent, and the measurement of HDL3-C by the fractionation method.

EXAMPLE 7

Quantification of HDL3-C in a Sample

The concentration of HDL3-C contained in each of 5 human fresh serum samples was determined, by the fractionation method, and by the methods using each of the kits of Example 3(6) and Example 3(11) of the present invention in accordance with the procedures as described below.

(1) Quantification of HDL3-C by a Fractionation Method

HDL3 was separated from each of the samples by the method described in Journal of Lipid Research vol. 49, p. 1130-1136 (2008) (fractionation method), and cholesterol in the obtained HDL3 fraction was then measured using Determiner L TCII (manufactured by Kyowa Medex Co., Ltd.). Thus, the concentration of HDL3-C in each of the samples was determined.

(2) Quantification of HDL3-C Using the Kits of Example 3(6) and Example 3(11)

A serum standard solution having the concentration of HDL3-C of 16.1 mg/dL by the measurement according to the fractionation method, was used as a sample for preparation of a calibration curve. Employing Hitachi 7170S Auto Analyzer, the reaction absorbance of the sample for preparation of a calibration curve was measured by the same measurement method as that described in Example 2(1), using the kit of Example 3(6). Thereafter, a calibration curve showing the relationship between the HDL3-C concentration and the reaction absorbance was prepared.

Five human serum samples were used instead of the aforementioned sample for a preparation of a calibration curve, and the measurement was carried out by the same method as that described in Example 2(1). Based on the obtained measurement value and the previously prepared calibration curve, the concentration of HDL3-C in each of the samples was determined.

The concentration of HDL3-C contained in each of the same 5 human serum samples as described above was determined by the same method as described above, using the kit of Example 3(11) instead of the kit of Example 3(6).

The HDL3-C concentrations determined by the fractionation method and the HDL3-C concentrations determined using the kits of Example 3(6) and Example 3(11) are shown in Table 4.

TABLE 4

| | HDL3-C concentration (mg/dL) | | |
|---|---|---|---|
| Sample | Fractionation method | Example 3 (6) | Example 3 (11) |
| Sample 1 | 17.3 | 16.1 | 17.2 |
| Sample 2 | 14.2 | 14.4 | 15.5 |
| Sample 3 | 10.1 | 9.9 | 10.1 |
| Sample 4 | 19.9 | 18.1 | 20.5 |
| Sample 5 | 6.7 | 8.4 | 8.3 |

From the results shown in Table 4, it proved that the HDL3-C concentration determined by the measurement method using the kit of the present invention was almost identical to the HDL3-C concentration determined by the fractionation method. Therefore, it proved that the measurement method using the kit of the present invention can precisely measure HDL3-C in human serum.

INDUSTRIAL APPLICABILITY

According to the present invention, a method, a reagent and a kit for measuring cholesterol in an HDL subfraction, which are effective for the diagnosis of coronary heart disease and the like, are provided.

The invention claimed is:

1. A method for determining cholesterol in high-density lipoprotein 3 (HDL3) contained in a sample, which comprises
reacting, in an aqueous medium containing (a) a divalent metal salt, (b) an alkali metal sulfate, and (c) dextran sulfate or a salt thereof, the sample with (1) a combination of a cholesterol ester hydrolase and a cholesterol oxidase or (2) a combination of a cholesterol ester hydrolase, an oxidized coenzyme and a cholesterol dehydrogenase; wherein the concentration of alkali metal ions derived from the alkali metal sulfate in the reaction solution is 5 to 21 mmol/L;
measuring a substance formed or consumed in the reaction;
correlating a calibration curve indicating a relationship between a concentration of cholesterol in HDL3 and an information amount derived from the substance formed or consumed with the measurement value of the substance formed or consumed; and
determining the concentration of cholesterol in HDL3 contained in the sample, wherein
the method is carried out without separating and removing lipoproteins other than HDL3 from the sample.

2. The method according to claim 1, wherein the divalent metal salt is a magnesium salt or a calcium salt.

3. The method according to claim 2, wherein the concentration of the dextran sulfate or a salt thereof in the reaction solution is 0.75 to 2.6 g/L.

4. The method according to claim 1, wherein the concentration of divalent metal ions derived from the divalent metal salt in the reaction solution is 12 to 20 mmol/L.

5. A method for determining cholesterol in high-density lipoprotein 2 (HDL2) contained in a sample, which comprises the following steps:
(1) a step of measuring cholesterol in a high-density lipoprotein (HDL) contained in the sample;
(2) a step of measuring cholesterol in HDL3 contained in the sample by the method according to claim 4; and
(3) a step of subtracting a measurement value obtained by the measurement in the step (2) from a measurement value obtained by the measurement in the step (1).

* * * * *